(12) United States Patent
Zenke et al.

(10) Patent No.: US 6,455,518 B2
(45) Date of Patent: *Sep. 24, 2002

(54) PHARMACEUTICAL COMPOSITIONS FOR THE TREATMENT OF TRANSPLANT REJECTION, AUTOIMMUNE OR INFLAMMATORY CONDITIONS COMPRISING CYCLOSPORIN A AND 40-O-(2-HYDROXYETHYL)-RAPAMYCIN

(75) Inventors: Gerhard Zenke, Rheinfelden (DE); Hendrik Schuurman, Basel; Barbara Haeberlin, Riehen, both of (CH); Armin Meinzer, Buggingen (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/758,301

(22) Filed: Jan. 11, 2001

Related U.S. Application Data

(63) Continuation of application No. 09/230,618, filed as application No. PCT/EP97/04123 on Jul. 29, 1997, now Pat. No. 6,239,124.

(30) Foreign Application Priority Data

Jul. 30, 1996 (GB) ............................................. 9615942
Mar. 19, 1997 (GB) ............................................. 9705684

(51) Int. Cl.$^7$ ........................ A61K 31/33; A61K 31/26; A61K 31/70
(52) U.S. Cl. ........................ 514/183; 514/514; 514/516; 514/31
(58) Field of Search ................................ 514/183, 514, 514/516, 31

(56) References Cited

U.S. PATENT DOCUMENTS

| | | | | |
|---|---|---|---|---|
| 5,286,730 A | * | 2/1994 | Caufield et al. ............. | 514/291 |
| 5,665,772 A | | 9/1997 | Cottens et al. .............. | 514/514 |
| 6,239,124 B1 | * | 5/2001 | Zenke et al. ................ | 514/183 |

FOREIGN PATENT DOCUMENTS

| | | |
|---|---|---|
| EP | 0 184 162 | 6/1986 |
| EP | 401 747 | 12/1990 |
| EP | 0533433 | * 3/1993 |
| EP | 0 562 853 | 3/1993 |
| EP | 0 583 925 | 8/1993 |
| EP | 2 278 780 A | 12/1994 |
| WO | 94 09010 | 4/1994 |
| WO | 97 25977 | 7/1997 |
| WO | WO 97/35575 | 10/1997 |

OTHER PUBLICATIONS

Kimball et al., Transplant. Proc., 23(1), 1027–1028, (1991).
Whiting et al., Transplant., 52(2), 203–208, (1991).
Kahan et al., Transplant. Proc., 23(1), 1090–1091, (1991).
Kahan et al., Transplant. 51(1), 232–239, (1991).
Warner et al., Inflam. Res., 44, Suppl. 2, S205–S206, (1995).
Yakimets, et al., Transplant., 5616) 1293–1298 (1993).
Stepkowski et al., Transplantation, vol. 62, No. 7, 986–994, Oct. 15, 1996.
Kahan et al., Therapeu. Drug. Monitor., 17:672–675, 1995.
DiJoseph et al., Transplantation, vol. 62, No. 8, 1109–1112, Oct. 27, 1996.
Granger et al., Transplantation, vol. 59, No. 2, 183–186, Jan. 27, 1995.
Shuurman H.J. et al., Transplantation, vol. 64, No. 1, pp. 32–35 (1997).
Tu Y. et al., Transplantation, vol. 59/2, pp. 177–183 (1995).
Schuler W. et al., Transplantation, vol. 64, No. 1, pp. 36–42 (1997).

* cited by examiner

*Primary Examiner*—Kevin E. Weddington
(74) *Attorney, Agent, or Firm*—Gabriel Lopez

(57) ABSTRACT

A synergistic combination of an IL-2 transcription inhibitor (e.g., cyclosporin A or FK506) and 40-O-(2-hydroxyethyl)-rapamycin is provided, which is useful in the treatment and prevention of transplant rejection and also certain autoimmune and inflammatory diseases, together with novel pharmaceutical compositions comprising an IL-2 transcription inhibitor in combination with a rapamycin, e.g., 40-O-(2-hydroxyethyl)-rapamycin.

20 Claims, No Drawings

PHARMACEUTICAL COMPOSITIONS FOR THE TREATMENT OF TRANSPLANT REJECTION, AUTOIMMUNE OR INFLAMMATORY CONDITIONS COMPRISING CYCLOSPORIN A AND 40-O-(2-HYDROXYETHYL)-RAPAMYCIN

This is a continuation of Ser. No. 09/230,618, Jan. 28, 1999, now U.S. Pat. No. 6,239,124, which is a 371 of PCT/EP97/04123, Jul. 29, 1997.

This invention relates to certain novel pharmaceutical compositions comprising a rapamycin, e.g., 40-O-(2-hydroxyethyl)-rapamycin, and an IL-2 transcription inhibitor, in particular FK-506 or cyclosporin A, and to synergistic combinations of an IL-2 transcription inhibitor and 40-O-(2-hydroxyethyl)-rapamycin.

40-O-(2-hydroxyethyl)-rapamycin has the following structure:

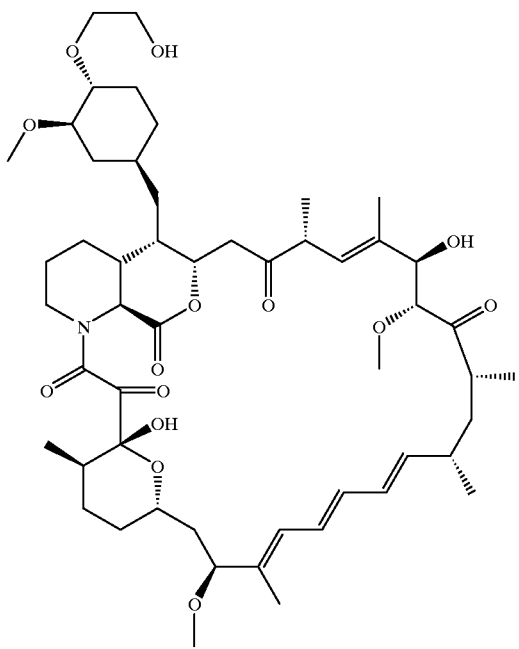

This compound is further described in WO 94/09010, example 8. 40-O-(2-hydroxyethyl)-rapamycin is a semisynthetic derivative of rapamycin. The structure of rapamycin is given in Kesseler, H., et al.; 1993; *Helv Chim. Acta*; 76: 117, and numerous immunosuppressive derivatives and analogues of rapamycin are known. Rapamycin is an immunosuppressant, but although it was first discovered over twenty years ago, it has yet to reach the market. Rapamycin is difficult to formulate, being poorly soluble and having poor oral bioavailability. The 40-O-(2-hydroxyethyl) derivative of rapamycin has improved formulation and pharmacokinetic properties. However, both rapamycin and 40-O-(2-hydroxyethyl)-rapamycin exhibit side effects on in vivo administration at higher dosages.

Cyclosporin A (also known as Ciclosporin or Cyclosporine) is an immunosuppressive, cyclic undecapeptide. Its structure is disclosed, e.g., in The Merck Index, 11th Edition; Merck & Co., Inc.; Rahway, N.J., USA (1989) under listing 2759. Formulations of cyclosporin A are available commercially under the trademark SANDIMMUN or SANDIMMUNE, and a microemulsion preconcentrate formulation of cyclosporin A is sold under the trademark NEORAL or OPTORAL. Cyclosporin A is widely used as an immunosuppressant, e.g., in the prevention and treatment of graft rejection following organ transplant and of graft versus host disease, e.g., following bone marrow transplant. At higher dosages, however, it may affect kidney and liver function. Moreover, cyclosporin A is difficult to formulate, as it is essentially insoluble in most pharmaceutically acceptable solvents, e.g. aqueous pharmaceutical systems, and its oral bioavailability in most formulations is variable. Finally, although cyclosporin A is highly effective in preventing and treating acute rejection episodes in transplant patients and hence contributes to long-term graft survival, chronic rejection, manifest as arteriostenosis due to vascular smooth muscle proliferation in the graft (graft-vessel disease), remains a serious problem for some patients after transplantation, for example heart transplant recipients. Cyclosporin A, which inhibits primarily T-cells, is also not particularly effective to prevent antibody-mediated rejection as is seen following xenotransplantation.

FK506 is a macrolide immunosuppressant produceable by *Streptomyces tsukubaensis* No 9993. The structure of FK506 is given in the appendix to the Merck Index, supra, as item A5. FK506 is also used as an immunosuppressant. Although it is structurally very different from cyclosporin A, it has a similar mechanism of action, i.e., inhibition of T-cells via cytokine suppression, in particular IL-2 suppression. It is somewhat more potent than cyclosporin A, but also more toxic, and is also difficult to formulate, having low solubility and variable bioavailability and metabolism.

Immunosuppressive compounds whose immunosuppressive activity derives principally or in significant part from their direct or indirect inhibition of IL-2 gene transcription (e.g., corticosteroids, ascomycins, and cyclosporins; in particular cyclosporin A, FK506, and their various immunosuppressive derivatives and analogues; especially compounds which are at at least as active as cyclosporin A in an L-2 reporter gene assay) are hereinafter referred to as "IL-2 transcription inhibitors".

It is now surprisingly discovered that IL-2 transcription inhibitors and 40-O-(2-hydroxyethyl)-rapamycin, in particular cyclosporin A and 40-O-(2-hydroxyethyl)-rapamycin, act synergistically, so that effective immunosuppression is seen upon co-administration at dosages which would be well below the effective dosages individually. Moreover, this synergistic combination is useful to treat, e.g. ameliorate, or prevent not only acute rejection, but also chronic rejection and xenograft rejection. Co-administration of the two compounds in synergistically effective amounts allows for significantly lower dosages of each compound in immunosuppression, thereby reducing the side effects, and by preventing chronic rejection and xenograft rejection, enhances the pharmaceutical utility of the treatment.

Synergy is calculated as described in Berenbaum, Clin. Exp. Immunol. (1977) 28: 1, using an interaction term to correct for differences in mechanism between the two drugs, as described in Chou, et al. Transpl. Proc. (1994) 26: 3043. The index of synergy is calculated as $$\frac{\text{Dose of } A}{A_E} + \frac{\text{Dose of } B}{B_E} + \frac{(\text{Dose } A)\times(\text{Dose } B)}{A_E \times B_E}$$

in which the doses of the compounds A and B represent those used in a particular combination, and $A_E$ and $B_E$ are the individual doses of A and B respectively giving the same effect. If the result is less than 1, there is synergy; if the result is 1, the effect is additive; if the result is greater than 1, A and B are antagonistic. As described below, cyclosporin A and 40-O-(2-hydroxyethyl)-rapamycin show an index of synergy of from about 0.3 to about 0.7 in vivo, and about 0.8 in vitro. By plotting an isobologram of dose of $A/A_E$ vs. dose of $B/B_E$, the combination of maximum synergy can be determined. The synergistic ratio expressed in terms of the ratio by weight of the two compositions at synergistic amounts along this isobologram, especially at or near the point of maximum synergy, can then be used to determine formulations containing an optimally synergistic ratio of the two compounds.

Remarkably, IL-2 transcription inhibitors and 40-O-(2-hydroxyethyl)-rapamycin exhibit synergy at two levels. At a mechanistic level e.g., as seen in in-vitro results, the intrinsic immunosuppressive activity of the two compounds is synergistically enhanced on co-administration. Moreover, at a pharmacokinetic level, the observed blood levels of both compounds on co-administration are significantly improved over blood levels achieved by administration of either compound individually and correspondingly, the observed in vivo synergy is greater even than would be predicted based on the in vitro results. The mechanistic synergy in combination with the pharmacokinetic interaction synergy is extremely surprising, and indeed, this combination of drugs is believed to be the first reported wherein significant synergy exists at both the mechanistic level and the pharmacokinetic level. The practical effect of this from the patient's perspective is that both drugs are more effective, at lower dosages, with fewer side effects, and improved bioavailability. Surprisingly, it is feasible that the drugs can be formulated into a fixed combination, which greatly enhances the convenience for the patient.

The indications for which this combination is of interest include in particular autoimmune and inflammatory conditions and conditions associated with or causal to transplant rejection, e.g., treatment (including amelioration, reduction, elimination or cure of etiology or symptoms) or prevention (including substantial or complete restriction, prophylaxis or avoidance) of the following:

a) Acute organ or tissue transplant rejection, e.g. treatment of recipients of e.g. heart, lung, combined heart-lung, liver, kidney, pancreatic, skin, bowel, or corneal transplants, especially prevention and/or treatment of T-cell mediated rejection, as well as graft-versus-host disease, such as following bone marrow transplantation.

b) Chronic rejection of a transplanted organ, in particular, prevention of graft vessel disease, e.g., characterized by stenosis of the arteries of the graft as a result of intima thickening due to smooth muscle cell proliferation and associated effects.

c) Xenograft rejection, including the acute, hyperacute or chronic rejection of an organ occurring when the organ donor is of a different species from the recipient, most especially rejection mediated by Bells or antibody-mediated rejection.

d) Autoimmune disease and inflammatory conditions, in particular inflammatory conditions with an etiology including an immunological or autoimmune component such as arthritis (for example rheumatoid arthritis, arthritis chronica progrediente and arthritis deformans) and other rheumatic diseases. Specific autoimmune diseases for which the synergistic combination of the invention may be employed include, autoimmune hematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, (autoimmune) inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy) and juvenile dermatomyositis. Autoimmune and inflammatory conditions of the skin are also considered to be amenable to treatment and prevention using the synergistic combination of the invention, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin, as are inflammatory conditions of the lungs and airways including asthma, allergies, and pneumoconiosis.

The invention thus provides products and methods for co-administration of an IL-2 transcription inhibitor (e.g., cyclosporin A or FK506) and 40-O-(2-hydroxyethyl)-rapamycin, especially cyclosporin A and 40-O-(2-hydroxyethyl)-rapamycin, at synergistically effective dosages, e.g., 1. A method of treatment or prevention of a condition as described above, e.g., an autoimmune or inflammatory condition or transplant rejection, especially chronic rejection or xenograft rejection, in a subject suffering from or at risk for such condition or rejection, for example a patient suffering from an autoimmune or inflammatory condition or a transplant recipient, comprising co-administering synergistically effective amounts of cyclosporin A and 40-O-(2-hydroxyethyl)-rapamycin.

2. The use of an IL-2 transcription inhibitor (e.g., cyclosporin A or FK506, especially cyclosporin A) in the manufacture of a medicament for co-administration in synergistically effective amounts with 40-O-(2-hydroxyethyl)-rapamycin, e.g., for use in the treatment or prevention of a condition as described above, e.g., an autoimmune or inflammatory condition, or transplant rejection, especially chronic rejection or xenograft rejection.

3. The use of 40-O-(2-hydroxyethyl)-rapamycin in the manufacture of a medicament for co-administration in synergistically effective amounts with an IL-2 transcription inhibitor (e.g., cyclosporin A or FK506, especially cyclosporin A), e.g., for use in the treatment or prevention of a condition as described above, e.g., an autoimmune or inflammatory condition, or transplant rejection, especially chronic rejection or xenograft rejection.

4. A kit of parts comprising an IL-2 transcription inhibitor (e.g., cyclosporin A or FK506, especially cyclosporin A) and 40-O-(2-hydroxyethyl)-rapamycin in separate unit dosage forms, preferably wherein said unit dosage forms are suitable for administration of the two compounds in synergistically effective amounts, together with instructions for use, e.g., in treatment or prevention of a condition as described above, e.g., an autoimmune or inflammatory condition, or transplant rejection, especially chronic rejection or xenograft rejection. The kit may further comprise means for facilitating compliance with the administration of the compounds, e.g. a label or drawings.

5. The use of an IL-2 transcription inhibitor (e.g., cyclosporin A or FK506, especially cyclosporin A) in the manufacture of a pharmaceutical kit which is to be used for facilitating co-administration with 40-O-(2-hydroxyethyl)-rapamycin.

6. The use of 40-O-(2-hydroxyethyl)-rapamycin in the manufacture of a pharmaceutical kit which is to be used for facilitating co-administration with an IL-2 transcription inhibitor (e.g., cyclosporin A or FK506, especially cyclosporin A).

7. An IL-2 transcription inhibitor (e.g., cyclosporin A or FK506, especially cyclosporin A) and 40-O-(2-hydroxyethyl)-rapamycin as a combined pharmaceutical preparation for simultaneous, separate or sequential use, preferably in synergistically effective amounts, e.g., for the treatment or prevention of a condition as described above, e.g., an autoimmune or inflammatory condition, or transplant rejection, especially chronic rejection or xenograft rejection.

8. A pharmaceutical composition comprising an IL-2 transcription inhibitor (e.g., cyclosporin A or FK506, especially cyclosporin A) and 40-O-(2-hydroxyethyl)-rapamycin, e.g., in synergistically effective amounts, in combination or association with a pharmaceutically acceptable diluent or carrier, e.g. for use in treatment or prevention of a condition as described above, e.g., the treatment or prevention of an autoimmune or inflammatory condition, or transplant rejection, especially chronic rejection or xenograft rejection.

By "synergistically effective amounts" is meant an amount of IL-2 transcription inhibitor and an amount of 40-O-(2-hydroxyethyl)-rapamycin which are individually below their respective effective dosages for the relevant indication, but which are pharmaceutically active on co-administration, e.g., in a synergistic ratio, for example as calculated above. Furthermore, "synergistically effective amounts" may mean an amount of IL-2 transcription inhibitor and an amount of 40-O-(2-hydroxyethyl)-rapamycin which are individually equal to their respective effective dosages for the relevant indication, and which result in a more than additive effect. The molar amount of 40-O-(2-hydroxyethyl)-rapamycin present is significantly less, preferably one half or less, than the amount of IL-2 transcription inhibitor. Synergistic ratios of cyclosporin A to 40-O-(2-hydroxyethyl)-rapamycin by weight are thus suitably from 2:1 to 180: 1, preferably from 5:1 to 50:1, most preferably from 10:1 to 20:1, e.g. about 16:1. Synergistic ratios of cyclosporin A to 40-O-(2-hydroxyethyl)-rapamycin by weight are for example 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1 or greater than 50:1, e.g. 60:1.

Absolute dosages of the compounds will vary depending on the individual, the route of administration and the nature and severity of the condition to be treated. For example, in prevention and treatment of transplant rejection, an initial dosage of about 2–3 times the maintenance dosage is suitably administered 4–12 hours prior to transplantation, followed by a daily dosage of about 2–3 times the maintenance dosage for a period of from 1–2 weeks, and subsequently the dose is gradually tapered down at a rate of about 5% per week to reach the maintenance dosage. In general, synergistically effective amounts of 40-O-(2-hydroxyethyl)-rapamycin and cyclosporin A on oral administration for use in prevention and treatment of transplant rejection in larger animals, e.g., man, are amounts of cyclosporin A of up to 5 mg/kg/day, e.g., from 0.5 mg/kg/day to 3 mg/kg/day, preferably about 1.5 mg/kg/day, in combination or co-administration with amounts of 40-O-(2-hydroxyethyl)-rapamycin of up to 2.5 mg/kg/day, e.g., from 0.01 mg/kg/day to 1 mg/kg/day, preferably about 0.1 mg/kg/day, in a synergistic ratio, as described. Suitable unit dosage forms for oral co-administration of these compounds thus may contain on the order of from 0.1 to 70 mg, preferably 1.0 to 10.0 mg, of 40-O-(2-hydroxyethyl)-rapamycin and from 1 to 200 mg, preferably 10 to 100 mg of cyclosporin A. The daily dosage for oral administration is preferably taken in a single dose, but may be spread out over two, three or four dosages per day. For i.v. administration, the effective dosage is lower than that required for oral administration, e.g. about one third the oral dosage. Because the bioavailability of cyclosporin A and 40-O-(2-hydroxyethyl)-rapamycin is subject to a certain degree of individual variability, it may be advisable to measure blood levels of the cyclosporin and/or 40-O-(2-hydroxyethyl)-rapamycin, preferably using monoclonal antibody-based assays as are known in the art for both cyclosporin A and 40-(2-hydroxyethyl)-rapamycin, especially during the first few months, in order to establish an optimal maintenance dosage for the individual patient.

By "co-administration" is meant administration of the 40-O-(2-hydroxyethyl)-rapamycin and the IL-2 transcription inhibitor, e.g., cyclosporin A, together or at substantially the same time (e.g., within fifteen minutes or less), either in the same vehicle or in separate vehicles, so that upon oral administration, for example, both compounds are present simultaneously in the stomach. Preferably, the compounds are administered as a fixed combination, e.g., a pharmaceutical formulation according to 5 above.

Pharmaceutical compositions under 6 above include compositions suitable for administration by any conventional route, in particular compositions suitable for administration enterally, e.g. orally, for example in the form of solutions for drinking, tablets or capsules, or parenterally, for example in the form of injectable solutions or suspensions. Normally for systemic administration oral dosage forms are preferred, although for some conditions, for example for prevention of rejection of liver transplants, an intravenously injectable form is desirable. Pharmaceutical compositions under 6 above also include compositions suitable for topical administration e.g., in the form of a dermal cream, ointment, gel or like preparation, especially in combination or association with penetration enhancing agents, e.g., for the treatment of autoimmune or inflammatory conditions of the skin, as well as composition in the form of an ocular cream, gel or eye-drop preparation, e.g. for the purposes of application to the eye, and inhalable compositions, e.g., for use in treatment of autoimmune or inflammatory conditions of the lungs and airways.

Pharmaceutical compositions under 6 above, e.g., for oral administration, are suitably emulsions, microemulsions, emulsion preconcentrates or microemulsion preconcentrates, or solid dispersions, especially water-in-oil microemulsion preconcentrates or oil-in-water microemulsions, comprising the IL-2 transcription inhibitor (e.g., cyclosporin A or FK506, especially cyclosporin A) and 40-O-(2-hydroxyethyl)-rapamycin in a synergistic ratio.

An emulsion preconcentrate is a formulation which forms an emulsion in an aqueous medium, e.g., water or gastric juice. An emulsion is an opaque or substantially opaque colloidal dispersion that is formed when its components are brought into contact, e.g., a composition containing dispersed particles of a size greater than about 2000 A (200 nm) in diameter, e.g. as described in GB 2 270 842, the contents of which are incorporated herein by reference. A microemulsion preconcentrate is a formulation which spontaneously forms a microemulsion in an aqueous medium, e.g., water or gastric juice. A microemulsion is a transparent or slightly opalescent colloidal dispersion that is formed spontaneously or substantially spontaneously when its components are brought into contact, e.g., a thermodynamically stable composition containing dispersed droplets of a size less than about 2000 A (200 nm) in diameter, generally less than 1500 A (150 nm), typically from 30 to 1000 A (3 to 100 nm), for example as described in GB 2 222 770 A.

Preferred compositions are those having cyclosporin A and 40-O-(2-hydroxyethyl)-rapamycin in a synergistically effective ratio in an oil-in-water microemulsion or in a water-in-oil microemulsion preconcentrate capable of forming a microemulsion, comprising a hydrophilic phase, a lipophilic phase, and a surfactant, e.g. wherein the hydrophilic phase, lipophilic phase, and surfactant are as described in GB 2 222 770, GB 2 257 359 or in WO 96/13273 the contents of which publications are incorporated herein by reference. The hydrophilic phase may comprise 5 to 50% by weight of the composition, e.g. 10 to 50%; preferably 15 to 40% by weight. The lipophilic phase may comprise 5 to 85% by weight of the composition, e.g. 10 to 85%; preferably 15 to 70% by weight. The surfactant may comprise 5 to 80% by weight of the composition; preferably 10 to 70% by weight.

Suitable components for the hydrophilic phase include components described in GB 2 222 770, for example a pharmaceutically acceptable $C_{1-5}$ alkyl or tetrahydrofurfuryl di- or partial-ether of a low molecular weight mono-or poly-oxy-alkanediol, e.g. diethylene glycol monoethyl ether available commercially under the trade name Transcutol, or tetrahydrofurfuryl alcohol polyethylene glycol ether available commercially under the trade name Glycofurol; or (especially) 1,2-propylene glycol; or dimethylisosorbide, and may optionally further include lower alkanols, e.g., ethanol.

Suitable components for the lipophilic phase include medium chain fatty acid triglycerides, mixed mono-, di-, and tri-glycerides, and transesterified ethoxylated vegetable oils, especially purified mono-, di-, tri-glycerides from glycerolysed corn oil e.g., free or substantially free from glycerol and saturated fatty acid components, e.g. as described and claimed in GB 2 284 615 B, the contents of which are incorporated herein by reference.

In one embodiment the lipophilic phase comprises a transesterification product of corn oil and glycerol having a saturated fatty acid content of mono-, di-, and tri-glycerides, and having a glycerol content less than 10% by weight, e.g. less than 5% such as 2% or less. The transesterification product comprises
  i) from about 25% to about 50% by weight, e.g. 30% to 40%, of mono-glycerides; from about 30% to about 60%, e.g. about 45% to about 55%, by weight of di-glycerides; and at least 5% by weight of tri-glycerides, e.g. about 7.5 to about 15%;
  ii) a linoleic acid, oleic acid and linolenic acid mono-, di- and tri-glyceride content of at least 85% by weight; and the total saturated fatty acid content of mono-, di-, and tri-glycerides is less than 10% by weight. In a preferred embodiment the transesterification product has a total palmitic acid and stearic acid content of mono-, di- and tri-gylcerides of less than 10% by weight.

Suitable surfactants include reaction products of natural or hydrogenated vegetable oils and ethylene glycol, e.g., polyethoxylated castor oils available for example under the trade mark CREMOPHOR (H. P. Fiedler, Lexikon der Hilfsstoffe für Pharmazie, Kosmetik und angrenzende Gebiete, Vol. 1, 3rd edition, 1989) e.g. CREMOPHOR RH 40 or EL; polyoxyethylene-glycerol-fatty acid esters, e.g. available under the trade mark TAGAT, e.g. TAGAT TO; and polyoxyethylene sorbitan fatty acid esters, e.g. mono-, di- and tri-lauryl, palmityl, stearyl and oleyl esters of the type known and available under the trade mark TWEEN, e.g. TWEEN 40 or TWEEN 80. These and other surfactants are also described in GB 2 222 770 and GB 2 257 359.

The compositions may optionally further comprise flavoring agents and/or antioxidants e.g. α-tocopherol typically in an amount of from 0.05% to about 5% by weight, preferably from about 0.1 to about 1% by weight based on the weight of the composition. The compositions may comprise acidic stabilizing agents, e.g. malonic acid, oxalic acid, citric acid or lactic acid e.g. in an amount of from 0.05% to about 5% by weight, preferably from about 0.1 to about 1% by weight based on the weight of the composition.

The pharmaceutical compositions are preferably compounded in unit dosage form, for example by filling into orally administrable capsule shells. The capsule shells may be soft or hard gelatine capsule shells. Stable soft gelatin capsules containing for example the cyclosporin A/40-O-(2-hydroxyethyl)-rapamycin compositions of this invention may be prepared in accordance with the method described in GB 2 282 586, the contents of which are incorporated herein by reference. If desired, however, the pharmaceutical compositions may be in drink solution form and may include water or any other aqueous system, to provide emulsion or microemulsion systems suitable for drinking.

Depending on the carrier material used, a solid dispersion in the form of a simple eutectic mixture, solid solution or solid micellar solution, glass suspension or glass solution of active agent/complex association may be formed which contains the IL-2 transcription inhibitor, e.g. cyclosporin A, with 40-O-(2-hydroxyethyl)-rapamycin in fine to molecularly dispersed form. Thus in one embodiment, a solid dispersion is formed which is a co-precipitate of the IL-2 transcription inhibitor, e.g. cyclosporin A, with 40-O-(2-hydroxyethyl)-rapamycin and a carrier medium e.g. as described in PCT/EP96/03066 the contents of which are incorporated herein by reference. In the solid dispersion, the IL-2 transcription inhibitor, e.g. cyclosporin A, and 40-O-(2-hydroxyethyl)-rapamycin are in amorphous or substantially amorphous form, and are physically bound to the carrier medium. The carrier medium, typically present in an amount of between 10 and 99.5% by weight based on the total weight of the composition, may comprise a water-soluble polymer for example hydroxypropylmethylcellulose, hydroxypropylmethylcellulose phthalate, polyvinylpyrrrolidone, hydroxypropylcellulose or derivatives thereof; a polyethylene glycol, for example PEG 2000, PEG 4000 or PEG 6000 (Handbook of Pharmaceutical Excipients); a saturated polyglycolised glyceride, available for example under the trade mark Gelucir, e.g. Gelucir 44/14, 53/10, 50/13, 42/12, or 35/10; or a cyclodextrin, for example a β-cyclodextrin or an α-cyclodextrin.

The carrier medium may further comprise a surfactant, for example as described above, or a polyoxyethylene-polyoxypropylene co-polymer or block co-polymer known, for example, under the trade names Pluronic or Poloxamer, e.g. Poloxamer 188; an ethoxylated cholesterin for example Solulan C24; a vitamin derivative, e.g. tocopherol polyethylene glycol succinate; sodium dodecylsulfate or sodium laurylsulfate; a bile acid or salt thereof, for example cholic acid, glycolic acid or a salt, e.g. sodium cholate; or lecithin. If present in the solid dispersion, the surfactant is generally in an amount of up to 20% by weight based on the total weight of the composition, e.g. 1 to 15% by weight. Other pharmaceutically acceptable excipients, e.g as described above, may be included in the solid dispersion as desired. When formulated as a solid dispersion, the compositions of this invention may be administered, for example, in tablet, capsule, granule or powder form, e.g. in a sachet.

In a further aspect the invention provides a pharmaceutical composition in the form of a microemulsion or a microemulsion preconcentrate, or a solid dispersion, e.g. as described herein, comprising (i) a rapamycin, e.g. rapamycin or 40-O-(2-hydroxyethyl)-rapamycin, and (ii) an IL-2 transcription inhibitor, e.g. cyclosporin A or FK 506, preferably in a synergistic ratio, e.g. as described above, for use in treatment or prevention of a condition as described above, e.g., the treatment or prevention of an autoimmune or inflammatory condition, or transplant rejection, especially chronic rejection or xenograft rejection, for example, A pharmaceutical composition having cyclosporin A and rapamycin in a synergistically effective ratio in an oil-in-water microemulsion or in a water-in-oil microemulsion preconcentrate capable of forming a microemulsion, comprising a hydrophilic phase, a lipophilic phase, and a surfactant, e.g. wherein the hydrophilic phase, lipophilic phase, and surfactant are as described in GB 2 222 770, GB 2 257 359 or in WO 96/13273 the contents of which publications are incorporated herein by reference, e.g., wherein the hydrophilic phase may comprise 5 to 50% by weight of the composition, e.g. 10 to 50%, preferably 15 to 40% by weight; the lipophilic phase may comprise 5 to 85% by weight of the composition, e.g. 10 to 85%, preferably 15 to 70% by weight; and the surfactant may comprise 5 to 80% by weight of the composition, preferably 10 to 70% by weight; or A pharmaceutical composition having cyclosporin A and rapamycin in a synergistically effective ratio in the form of a solid dispersion, e.g., a co-precipitate of cyclosporin A with rapamycin and a carrier medium e.g. as described above and in PCT/EP96/03066 the contents of which are incorporated herein by reference, and optionally further comprising a surfactant, for example as described above, e.g., in an amount of up to 20% by weight based on the total weight of the composition, e.g. 1 to 15% by weight. Microemulsions, microemulsion preconcentrates and solid dispersions comprising rapamycins other than 40-O-(2-hydroxyethyl)-rapamycin, e.g., rapamycin, may be formulated and used as described herein for compositions comprising 40-(2-hydroxyethyl)-rapamycin.

EXAMPLE 1

Synergism Between 40-O-(2-hydroxyethyl)-rapamycin and Cyclosporin A in Vitro

Synergy is shown between the 40-O-(2-hydroxyethyl)-rapamycin and cyclosporin A in the two-way mouse mixed lymphocyte reaction. Spleen cells of BALB/c and CBA mice ($1 \times 10^5$ from each strain) are cultured in duplicate in flat-bottom 96-well microtiter plates in the absence or presence of serially diluted compound in serum-free medium. After four days, $^3$H-thymidine is added. Sixteen hours later, the cells are harvested and $^3$H-thymidine incorporation is measured by liquid scintillation counting. Cell proliferation is assessed in the absence of compounds (100% value) or in the presence of serially diluted compounds or combinations of compounds. The maximum $^3$H thymidine incorporation (100% value) is around $240 \times 10^3$ cpm, and the background $^3$H-thymidine incorporation in unstimulated cells is around $5 \times 10^3$ cpm. Drug concentrations at which the maximum proliferative response is inhibited by 70% ($IC_{70}$) are calculated using a four-parameter logistic function. The $IC_{70}$ is 21 nM for cyclosporin A and 0.3 nM for 40-O-(2-hydroxyethyl)-rapamycin. In combinations, lymphocyte proliferation is determined in the presence of 0.05, 0.1, 0.2, 0.4, and 0.8 nM 40-O-(2-hydroxyethyl)-rapamycin, together with 2.5, 5.0, 10, 15, 20, or 25 nM cyclosporin A. For each drug combination, the respective $IC_{70}$ of each individual compound is calculated. These $IC_{70}$ values are converted into relative units with regard to the $IC_{70}$ value of the respective single drug treatment. These relative $IC_{70}$ units are graphically presented in an isobologram in FIG. 1. The concave nature of this isobologram indicates a synergistic action between the two compounds. The index of synergy at the most synergistic combination is calculated at a value of 0.8, e.g., a value of A/A of 0.19 for 40-O-(2-hydroxyethyl)-rapamycin and 0.52 for cyclosporin A.

EXAMPLE 2

Synergism Between 40-O-(2-hydroxyethyl)-rapamycin and Cyclosporin A in Vivo

Synergism in vivo is shown using orthotopic kidney and heterotopic heart allotransplantation models in male Lewis rats (RTI[1] haplotype) using donor organs from male DA rats (RTI$^a$ haplotype).

Kidney transplantation is followed by contralateral nephrectomy 7 days later: at nephrectomy, the graft is macroscopically inspected, and if rejection is macroscopically evident, the experiment is terminated. Surviving animals are monitored daily for clinical signs of renal dysfunction.

The heart allografts are transplanted into the abdomen, with anastomoses between the donor aorta and the recipient infrarenal abdominal aorta and between the donor right pulmonary artery and the recipient inferior vena cava. The abdomen is then palpated daily to determine if the graft is still beating; in case of cessation of heartbeat, the experiment is terminated.

In both the kidney and heart allograft experiments, the termination point in long term survivors is 100 days. In all cases, the graft is removed at autopsy, fixed in buffered formalin, and embedded in paraffin. Four micron thick sections stained with hematoxylin and eosin are read for signs of rejection and scored as "no rejection", or "marginal", "slight", "moderate", or "severe" cellular rejection based on the extent of mononuclear cell infiltration and damage to the parenchyma (tubules in the kidney, myocytes in the heart).

Lewis rats left untreated after transplantation reject a kidney allograft within 7 days, with a histology of severe cellular rejection; the heterotopic heart allograft in untreated recipients stops beating between day 7 and 10 post transplantation, with a similar histology of severe cellular rejection.

Cyclosporin A (NEORAL) and/or 40-O-(2-hydroxyethyl)-rapamycin are given daily orally in a microemulsion preconcentrate vehicle. Allograft survival data and histology are presented in Table 1. The minimum effective dose of cyclosporine A giving long term allograft survival is 5.0 mg/kg body weight, with a slight rejection in graft histology. For 40-O-(2-hydroxyethyl)-rapamycin, a dose of 5.0 mg/kg must be given for long term survival of a kidney allograft; this dose is not fully effective for heart allograft.

In combination treatment, a dose of 1.0 or 2.0 mg/kg cyclosporin A is combined with dosages of 0.5, 1.0 or 2.0 mg/kg 40-O-(2-hydroxyethyl)-rapamycin. Long term survival of the kidney allograft is seen at the lowest dosages of both compound; long term survival of the heart allograft at 1.0 mg/kg of each compound. Moreover, the histology of the long term surviving allografts is improved. Based on the minimum effective dose giving long term survival in single compound treatment (5.0 mg/kg for cyclosporin A, >5.0 mg/kg for 40-O-(2-hydroxyethyl)-rapamycin), the index of synergy for the kidney transplant model is about 0.3 (1.0 mg/kg cyclosporin A) to 0.5 (2.0 mg/kg cyclosporin A), and for heart transplant, <0.5 (1.0 mg/kg cyclosporin A) and <0.7 (2.0 mg/kg cyclosporin A). Thus the in vivo synergy of the compounds is even greater than would be predicted from the in vitro results.

TABLE 1

Effect of Neoral ® and 40-0-(2-hydroxyethyl)-rapamycin

| 40-0-(2-hydroxyethyl) rapamycin dose (mg/kg) | Neoral ® dose (mg/kg) | n | Survival (days) | Histology of rejection |
|---|---|---|---|---|
| KIDNEY | 2.5$^a$ | 3 | 7*,7*,7* | severe |
|  | 5.0$^a$ | 2 | 24≧100 | 24:severe |
|  |  |  |  | 100:slight |
|  | 7.5$^a$ | 6 | ≧90 (3x),≧100 (3x) | marginal, slight |
| 1.0 |  | 3 | 11,13,18 | moderate-severe |
| 2.5 |  | 4 | 14,15,18,18 | slight-moderate |
| 5.0 |  | 3 | 42,≧100,≧100 | moderate; ≧100 marginal |
| 0.5 | 1.0 | 3 | ≧100,≧100,≧100 | marginal-slight |
| 1.0 | 1.0 | 6 | 12,17,≧100 (4x) | marginal-slight |
| 2.0 | 1.0 | 3 | ≧64,≧100,≧100 | marginal |
| 0.5 | 2.0 | 3 | ≧100,≧100,≧100 | no rejection |
| 1.0 | 2.0 | 3 | ≧72,≧84≧100 | no rejection |
| 2.0 | 2.0 | 3 | ≧73,≧100,≧100 | no rejection |
| HEART | 2.5 | 3 | 10,10,14 | severe |
|  | 5.0 | 3 | ≧100,≧100,≧100 | slight |
| 1.0 |  | 3 | 12,14,14 | severe |
| 2.5 |  | 6 | 16,18,22,25,27,≧28 | moderate |
| 5.0 |  | 2 | 22,23 | moderate |
| 0.5 | 1.0 | 3 | 18,18,19 | moderate |
| 1.0 | 1.0 | 5 | 18,≧93,≧93≧95≧,105 | slight-moderate |
| 2.0 | 1.0 | 3 | ≧91,≧91,≧92 | marginal |
| 1.0 | 2.0 | 3 | ≧78,≧92,≧106 | no rejection |
| 2.0 | 2.0 | 3 | ≧66,≧105,≧106 | no rejection |

$^a$14-day daily treatment

EXAMPLE 3

Pharmacokinetic Interaction $^3$H-labeled 40-O-(2-hydroxyethyl)-rapamycin is given to male rats together with $^{14}$C-labeled Cyclosporin A, either as an intravenous bolus (1 mg/kg and 3 mg/kg, respectively) or orally in microemulsion (1.5 mg/kg and 3 mg/kg, respectively). Whole blood concentrations of both compounds are determined by liquid chromatography-reversed isotope dilution (LC-RID). The interaction between 40-O-(2-hydroxyethyl)-rapamycin and Cyclosporin A is investigated by comparing the pharmacokinetics after coadministration with those obtained after administration of each test compound alone, with results as depicted in Tables 2 and 3.

TABLE 2

40-O-(2-hydroxyethyl)-rapamycin and Cyclosporin disposition after intravenous administration alone and in combination
Doses: 1 mg/kg [$^3$H]40-O-(2-hydroxyethyl)-rapamycin, 3 mg/kg [$^{14}$C] Cyclosporin (values are means ± SE)

| Parameter | | 40-O-(2-hydroxyethyl)-rapamycin alone | 40-O-(2-hydroxy-ethyl) rapamycin (with Cyclosporin) | Cyclosporin alone | Cyclosporin (with 40-O-(2-hydroxy-ethyl)-rapamycin) |
|---|---|---|---|---|---|
| AUC | $\mu$g-ml$^{-1}$-h | 0.82 ± 0.04 | 1.55 ± 0.16 | 12.5–19.0 | 11.9 ± 1.5 |
| $t_{1/2}$ | h | 60 ± 10 | 56 ± 7 | 16–19 | 24 ± 1 |
| CL | ml/min | 8.2 ± 0.3 | 3.2 ± 0.3 | 0.7–1.4 | 1.3 ± 0.1 |
| V | l/kg | 52 ± 3 | 25 ± 3 | 2.7–4.5 | 3.3 ± 0.3 |

TABLE 3

Pharmacokinetics after oral administration alone and in combination
Doses: 1.5 mg/kg [$^3$H], 3 mg/kg [$^{14}$C]Cyclosporin (values are means ± SE)

| Parameter | | 40-O-(2-hydroxyethyl)-rapamycin alone | 40-O-(2-hydroxy-ethyl)-rapamycin (with Cyclosporin) | Cyclosporin alone | Cyclosporin with 40-O-(2-hydroxy-ethyl) rapamycin |
|---|---|---|---|---|---|
| $C_{max}$ | ng/ml | 16.7 ± 4.6 | 27.4 ± 7.3 | 228 ± 111 | 438 ± 247 |
| $t_{max}$ | h | 1.6 ± 0.7 | 0.8 ± 0.2 | 0.5 ± 0 | 3.5 ± 2.3 |
| $t_{1/2}$ | h | 61 ± 5 | 30 ± 6 | 12 ± 1 | 17 ± 3 |
| AUC | $\mu$g-ml$^{-1}$-h | 0.18 ± 0.06 | 0.31 ± 0.08 | 1.00 ± 0.20 | 3.10 ± 1.65 |

Clearance and volume of distribution of 40-O-(2-hydroxyethyl)-rapamycin are decreased (two-fold) by coadministration with Cyclosporin A; on the other hand, the disposition of Cyclosporin A is not affected by 40-O-(2-hydroxyethyl)-rapamycin. The increase of blood levels of 40-O-(2-hydroxyethyl)-rapamycin (two-fold) observed after oral coadministration with Cyclosporin may be attributed to the decrease in clearance and volume of distribution, whereas the two-fold increase of Cyclosporin blood levels after oral coadministration with 40-O-(2-hydroxyethyl)-rapamycin may be attributed to a higher absorption.

EXAMPLE 4

Combined Formulation

A soft gelatin capsule suitable for oral administration is prepared containing the following composition in a 500 mg dosage

| | |
|---|---|
| Cyclosporin A | 50 mg |
| 40-O-(2-hydroxyethyl)-rapamycin | 5 mg |
| 1,2-propylene glycol | 50 mg |
| ethanol absolute | 50 mg |
| corn oil mono-,di-,tri-glycerides | 154.5 mg |
| Cremophor RH40 | 190 mg |
| DL-alpha-tocopherol | 0.5 mg |
| Total | 500 mg |

The composition is stable and no precipitation is observed.

EXAMPLES 5 TO 9

Combined Formulations

Soft gelatin capsules suitable for oral administration are prepared containing the following compositions, each in a 500 mg dosage

| Example (amounts are in mg) | 5 | 6 | 7 | 8 | 9 |
|---|---|---|---|---|---|
| Cyclosporin A | 48 | 49 | 51 | 52 | 53 |
| 40-O-(2-hydroxyethyl)-rapamycin | 7 | 6 | 4 | 3 | 2 |
| 1,2-propylene glycol | 50 | 50 | 50 | 50 | 50 |
| ethanol absolute | 50 | 50 | 50 | 50 | 50 |
| corn oil mono-,di-,tri-glycerides | 154.5 | 154.5 | 154.5 | 154.5 | 154.5 |
| Cremophor RH40 | 190 | 190 | 190 | 190 | 190 |
| DL-alpha-tocopherol | 0.5 | 0.5 | 0.5 | 0.5 | 0.5 |

The compositions are stable and no precipitation is observed.

EXAMPLE 10

A solid dispersion formulation is prepared containing the following components in parts by weight:

| | |
|---|---|
| Cyclosporin A | 10 |
| 40-O-(2-hydroxyethyl)-rapamycin | 1 |
| HPMC 3 cps | 75 |
| Poloxamer 188 | 14 |

The components are dissolved in a 1:1 absolute ethanol/acetone mixture. The solvents are evaporated and the resulting dry residue milled to a fine powder with mean particle size around 0.1 to 0.4 nm. The fine powder is tabletted or filled into hard capsules.

What is claimed is:

1. An IL-2 transcription inhibitor and 40-O-(2-hydroxyethyl)-rapamycin as a combined pharamceutical preparation in the weight ratio 2:1 to 180:1 for simultaneous, separate, or sequential use in synergistically effective amounts.

2. A pharmaceutical composition comprising (I) an IL-2 transcription inhibitor and (II) 40-O-(2-hydroxyethyl)-rapamycin, wherein the weight ratio II is 2:1 to 180:1, in combination or association with a pharmaceutically acceptable diluent or carrier.

3. A composition of claim 2 in the form of a microemulsion or a microemulsion preconcentrate or a solid dispersion.

4. A composition of claim 3 which is a microemulsion preconcentrate formulation.

5. A composition of claim 3 which is a solid dispersion formulation.

6. A composition of claim 2 wherein I and II are present in an oil-in-water microemulsion preconcentrate comprising a hydrophilic phase, a lipophilic phase, and a surfactant.

7. A method of treating or preventing an autoimmune or inflammatory condition or transplant rejection in a subject suffering from or at risk for such condition or rejection, comprising co-administering synergistically effective amounts of (I) an IL-2 transcription inhibitor and (II) 40-O-(2-hydroxyethyl)-rapamycin in the weight ratio 2:1 to 180:1.

8. The method of claim 7 wherein the ratio is 5:1 to 60:1.

9. The method of claim 8 wherein the ratio is 10:1 to 20:1.

10. The method of claim 9 wherein the ratio is 16:1.

11. A method of treating or preventing chronic rejection of a heart, lung, or kidney transplant in a subject suffering from or at risk for such rejection, comprising co-administering together or at substantially the same time synergistically effective amounts of (I) an IL-2 transcription inhibitor and (II) 40-O-(2-hydroxyethyl)-rapamycin.

12. The method of claim 11 wherein the compounds are administered as a fixed combination.

13. The method of claim 11 wherein the weight ratio II is 5:1 to 50:1.

14. The method of claim 11 wherein the weight ratio is 10:1 to 20:1.

15. The method of claim 11 wherein the weight ratio is 16:1.

16. The method of claim 11 wherein compounds I and II are co-administered in combination or association with a pharmaceutically acceptable diluent or carrier.

17. The method of claim 16 wherein compounds I and II are co-administered in the form of a microemulsion, a microemulsion preconcentrate, or a solid dispersion.

18. A kit comprising (I) an IL-2 transcription inhibitor and (II) 40-O-(2-hydroxyethyl)-rapamycin in separate unit dosage forms, wherein said unit dosage forms are suitable for administrating I and II in synergistically effective amounts, wherein the weight ratio II is 2:1 to 180:1.

19. The method of using an IL-2 transcription inhibitor in the manufacture of a pharmaceutical kit of claim 18.

20. The method of using 40-O-(2-hydroxyethyl)-rapamycin in the manufacture of a pharmaceutical kit of claim 18.

* * * * *